United States Patent [19]
DiTullio et al.

[11] Patent Number: 5,843,705
[45] Date of Patent: Dec. 1, 1998

[54] TRANSGENICALLY PRODUCED ANTITHROMBIN III

[75] Inventors: Paul DiTullio, Framingham; Harry Meade, Newton; Edward S. Cole, Mendon, all of Mass.

[73] Assignee: Genzyme Transgenic Corporation, Framingham, Mass.

[21] Appl. No.: 391,743

[22] Filed: Feb. 21, 1995

[51] Int. Cl.$^6$ .............................. C12P 21/06; C12N 9/48
[52] U.S. Cl. .................. 435/69.1; 530/393; 530/392; 530/386; 530/380; 530/360; 530/412; 530/832; 514/8; 514/21; 435/320.1; 435/172.3; 435/172.1; 435/325; 800/2; 424/152.1; 424/535; 930/240
[58] Field of Search ............................... 435/320.1, 172.3, 435/240.2, 69.1, 325, 212, 172.1; 530/412, 360, 393, 70, 386, 832, 380; 514/8, 21; 800/2; 424/157.1, 535

[56] References Cited

U.S. PATENT DOCUMENTS

| | | | |
|---|---|---|---|
| 4,517,294 | 5/1985 | Bock et al. | 435/69.4 |
| 4,632,981 | 12/1986 | Bock et al. | 514/8 |
| 4,873,316 | 10/1989 | Meade et al. | 530/412 |
| 5,366,894 | 11/1994 | Clarke et al. | 435/320.1 |

OTHER PUBLICATIONS

Bock, S. et al., "Cloning and Expression of the cDNA for Human Antithrombin III", *Nucleic Acids Research*, vol. 10 (24), pp. 8113–8125 (1982).
Wall, R., "Transgenic Livestock: Progress and Prospects for the Future", *Theriogenology*, vol. 45, pp. 57–68 (1996).
Fan et al J. of Biol. Chem. 268(23):17588–96 1993.
Cole et al. J. of Cellular Biochemistry Supplement O (180). 1994 p. 265.
Edmundo et al J. of Cellular Biochemistry Supplement O(180) 1994 p. 265.
Wall Theriogenology 45:57–68 (1996).

*Primary Examiner*—Christopher S.F. Low
*Attorney, Agent, or Firm*—Louis Myers

[57] ABSTRACT

This invention relates to transgenically produced human Antithrombin III (tgATIII). The human ATIII produced by the transgenic process of the present invention has a monosaccharide composition which comprises N-acetylgalactosamine (GalNAc) along with fucose, N-acetylglucosamine, galactose, mannose, and N-acetylneuraminic acid/N-glycolyneuraminic acid. The monosaccharide composition differs with that of plasma derived ATIII (phATIII). It has been found that tgATIII has an increased clearance rate when compared to phATIII.

13 Claims, 11 Drawing Sheets

Sequence Listing

```
agaatttaccccaagatctcaaagacccactgaatactaaagagacctcattgtggttac        -263
aataatttggggactgggccaaaacttccgtgcatcccagccaagatctgtagctactgg        -203
acaatttcatttcctttatcagattgtgagttattcctgttaaaatgctccccagaattt        -143
ctggggacagaaaaataggaagaattcatttcctaatcatgcagatttctaggaattcaa         -83
atccactgttggtttttatttcaaaccacaaaattagcatgccattaaatactatatataa        -23
acagccactaaatcagatcattATCCATTCAGCTTCTCCTTCACTTCTTCTCCTCTACTT          37
TGGAAAAAAGgtaagaatctcagatataatttcagtgtatctgctactcatctttattt          97
ggactaggttaaaatgtagaaagaacataattgcttaaaatagatcttaaaaataagggt         157
gtttaagataaggtttacactattttcagcagatatgttaaaaaatagaagtgactataa        217
agacttgataaaaattataggtgactgcaa...................ttttttgccat        277
gaggtttgcaggatcttggttccctgaccagggatcaaacctgcactccctggaagcat         337
ggagtcttggacatttgtattatacactatctttggttccttttaaagggaagtaatttt        397
acttaaataagaaaatagattgacaagtaatacgctgtttcctcatcttcccattcacag        457
GAATCGAGAGCCATGAAGGTCCTCATCCTTGCCTGTCTGGTGGCTCTGGCCATTGCAAGA        517
     ****   M  K  V  L  I  L  A  C  L  V  A  L  A  I  A  R          16
GAGgtaaatacagaaaaaatgttgaaataatagactagtactgtctgcctatgtgtagaa        577
 E                                                                  17
atcacattaccaacatcataaatgtataaataatgcacaatctcagatttatttttaat         637
gctaagaaagtcatttatgttcatccactatctcaacagtatcctataggaccacaactc        697
tgggtcaagtgctttctatagtattgtaccatctgtaccatcaattcctaaagaaaaagg        757
aaaagaaaccaataagcaacagaccaacaagaaggaacacagacaagaacaaaaaatgag        817
taatattgtacaaatacaattgcacg..................ctgcaggaactaaa         877
gtgtttttttttctctctcttttagCAGGAAGAACTCAATGTAGTCGGTGAGgtaagat        937
                          Q  E  E  L  N  V  V  G  E              26
attttatacaaagaaaaaaattaatttaactgtaaaatagtaacagactctgatgatct         997
agcagaaaactcagctaattgtcaattttttattttccttatagACTGTGGAAAGCCTT        1057
                                              T  V  E  S  L        31
TCAAGCAGTGAGgtaagataatgttcattcagaggcaatttcccagatttagagcaataa      1117
 S  S  S  E                                                        35
aacactgtattatcttttttgtgttacattaattggcaacccactccagtactctt.....      1177
..............gacaaatatgaattttctttaaagctaaacctgatttattttt          1237
attttccaaagGAATCTATTACACACATCAATAAGgtaaaaccttcatatttaaacgta      1297
           E  S  I  T  H  I  N  K                                 43
cattttaaaaatttcatgtttgattttataacagcatttctttatgtgtgattttt          1357
ttttaccagAAAATTGAGAAGTTTCAAAGTGAGGAACAACAGCAAACAGAGgtaatttg      1417
         K  I  E  K  F  Q  S  E  E  Q  Q  Q  T  E                 57
ttcactatgagtatatttgagaagtattatgaaacataacacataaaagatttataata        1477
attatgttcagtctaagaatggtaatataagtgtcagtgtaagaaatgaaactttgaca       1537
```

Figure 10 a

```
aaatgaaaatattttaaagatagaaacacatttttaaacacataatcaaatttcagagta          1597
 tagaataaatacccaagaataactactggtatattcattttactaatggtatacctggct          1657
 ttaataaatgcatattagtaggaacaattccagactagggactg*gatcccttattcta          1717
 atgatggatatgctgataaagacagtagggtgacagtgtggcactaatcctaat.....          1777
 ................aaatggaagattttctttctctctcttcactgaattatgttttaa         1837
 aaagaggaggataattcatcatgaataacaattataactggattatggactgcaaaggca          1897
 ttggttttccttctttccagGATGAACTCCAGGATAAAATCCACCCCTTTGCCCAGGCAC          1957
                     D   E   L   Q   D   K   I   H   P   F   A   Q   A   Q     71
 AGTCTCTAGTCTATCCCTTCACTGGGCCCATCCCTAACAGCCTCCCACAAAACATCCTGC          2017
   S   L   V   Y   P   F   T   G   P   I   P   N   S   L   P   Q   N   I   L   P    91
 CTCTTACTCAAACCCCTGTGGTGGTGCCGCCTTTCCTTCAGCCTGAAATAATGGGAGTCC          2077
   L   T   Q   T   P   V   V   V   P   P   F   L   Q   P   E   I   M   G   V   P   111
 CCAAAGTGAAGGAGACTATGGTTCCTAAGCACAAAGAAATGCCCTTCCCTAAATATCCAG          2137
   K   V   K   E   T   M   V   P   K   H   K   E   M   P   F   P   K   Y   P   V   131
 TTGAGCCCTTTACTGAAAGCCAGAGCCTGACTCTCACTGATGTTGAAAAGCTGCACCTTC          2197
   E   P   F   T   E   S   Q   S   L   T   L   T   D   V   E   K   L   H   L   P   151
 CTCTGCCTCTGGTCCAGTCTTGGATGCACCAGCCTCCCCAGCCTCTTTCTCCAACCGTCA          2257
   L   P   L   V   Q   S   W   M   H   Q   P   P   Q   P   L   S   P   T   V   M   171
 TGTTTCCTCCTCAGTCCGTGCTGTCCCTTTCTCAGCCCAAAGTTCTGCCTGTTCCCCAGA          2317
   F   P   P   Q   S   V   L   S   L   S   Q   P   K   V   L   P   V   P   Q   K   191
 AAGCAGTGCCCCAGAGAGATATGCCCATCCAGGCCTTTCTGCTGTACCAGGAGCCTGTAC          2377
   A   V   P   Q   R   D   M   P   I   Q   A   F   L   L   Y   Q   E   P   V   L   211
 TTGGTCCTGTCCGGGGACCCTTCCCTATTCTTgtaagtctaaatttactaactgtgctgt          2437
   G   P   V   R   G   P   F   P   I   L                                        221
 ttaacttctgatgtttgtatgatatttgagtaattaagagccctacaaaaaaatcaataa          2497
 tgaatggttccaaaataagcatagctgagattaatgattctcagcattagttataaatag          2557
 aataagctggaaaaccttcacctcccctccaccaccagatccc.................          2617
 ...aaaaacaaaatactgaagatgcttatttcaatactcagggaaaattttcttgccaaa          2677
 aaggcaagaattgtataattcattcacttatttttatttttttaatttttaagGTCTAAG          2737
                                                       V   *   222
 AGGATTTCAAAGTGAATGCCCCCTCCTCACTTTTGgt....................caa          2797
 attggaaatggggtgagatgaagagttataacatataactaaatggacattgttctcta          2857
 ttccacagAATTGACTGCGACTGGAAATATGGCAACTTTTCAATCCTTGCATCATGCTAC          2917
 TAAGATAATTTTTAAATGAGTATACATGGAACAAAAAATGAAACTTTATTCCTTTATTTA          2977
 TTTTATGCTTTTTCATCTTAATTTGAATTTGAGTCATAAACCATATACTTTCAAAATGTT          3037
 AATTCAACATTAGCATAAAAGTTCAATTTTAACTTGGAAATATCATGAACATATCAAATT          3097
 ATGTATAAAAATAATTTCTGgaattgtgattattatttcttaagaatctatttcctaac          3157
 cagtcatttcaataaattaacccttaggcatatttaagttttcttgtctttattatattt          3217
 ttaaaaatgaaattggtctctttattgttaacttaaatttatctttgatgttaaaaatag          3277
 ctgtggaaaa                                                            3287
```

Figure 10 b

TRANSGENICALLY PRODUCED ANTITHROMBIN III

BACKGROUND OF THE INVENTION

A growing number of recombinant proteins are being developed for therapeutic and diagnostic applications; however, many of these proteins may be difficult or expensive to produce in a functional form in the required quantities using conventional methods. Conventional methods involve inserting the gene responsible for the production of a particular protein into host cells such as bacteria, yeast, or mammalian cells, and then growing the cells in culture media. The cultured cells then synthesize the desired protein. Traditional bacteria or yeast systems may be unable to produce many complex proteins in a functional form. While mammalian cells can reproduce complex proteins, they are generally difficult and expensive to grow, and produce only mg/L quantities of protein.

The application of transgenic technology to the commercial production of recombinant proteins in the milk of transgenic animals offers significant advantages over traditional methods of protein production. These advantages include a reduction in the total amount of required capital expenditures, elimination of the need for capital commitment to build facilities early in the product development life cycle, and lower direct production cost per unit for complex proteins. Of key importance is the likelihood that, for certain complex proteins, transgenic production may represent the only technologically and economically feasible method of commercial production.

Antithrombin III (ATIII) is a serine protease inhibitor which inhibits thrombin and the activated forms of factors X, VII, IX, XI, and XII. It is normally present in serum at levels of 14–20 mg/dL. Decreased levels of ATIII may be found in the serum of individuals who have either a hereditary deficiency of ATIII or an acquired deficiency, which can result from a number of pathologic conditions. The conventional treatment for hereditary ATIII deficiency is protein replacement therapy, which may also be effective in treating some acquired deficiencies.

Current methods of obtaining ATIII involves isolating the protease inhibitor from blood plasma. However, the use of plasma-based ATIII presents various problems due to the many components in plasma, including: variation between lots; immunogenicity problems; and biohazardous risks due to viral contamination.

A need exists to develope a method to produce ATIII without the inherent problems of the present process.

SUMMARY OF THE INVENTION

This invention relates to transgenically produced human Antithrombin III (tgATIII). The human ATIII (hATIII) produced by the transgenic process of the present invention has a monosaccharide composition which comprises N-acetylgalactosamine (GaINAc) along with fucose, N-acetylglucosamine, galactose, mannose, and N-acetylneuraminic acid/N-glycolyneuraminic acid. The monosaccharide composition differs with that of human plasma derived ATIII (phATIII). It has been found that tgATIII has an increased clearance rate when compared to phATIII.

BRIEF DESCRIPTION OF THE DRAWINGS

FIGS. 10a and 10b depict the nucleotide sequence and the corresponding amino acid sequence of human antithrombin III.

DETAILED DESCRIPTION OF THE INVENTION

Figure 1:
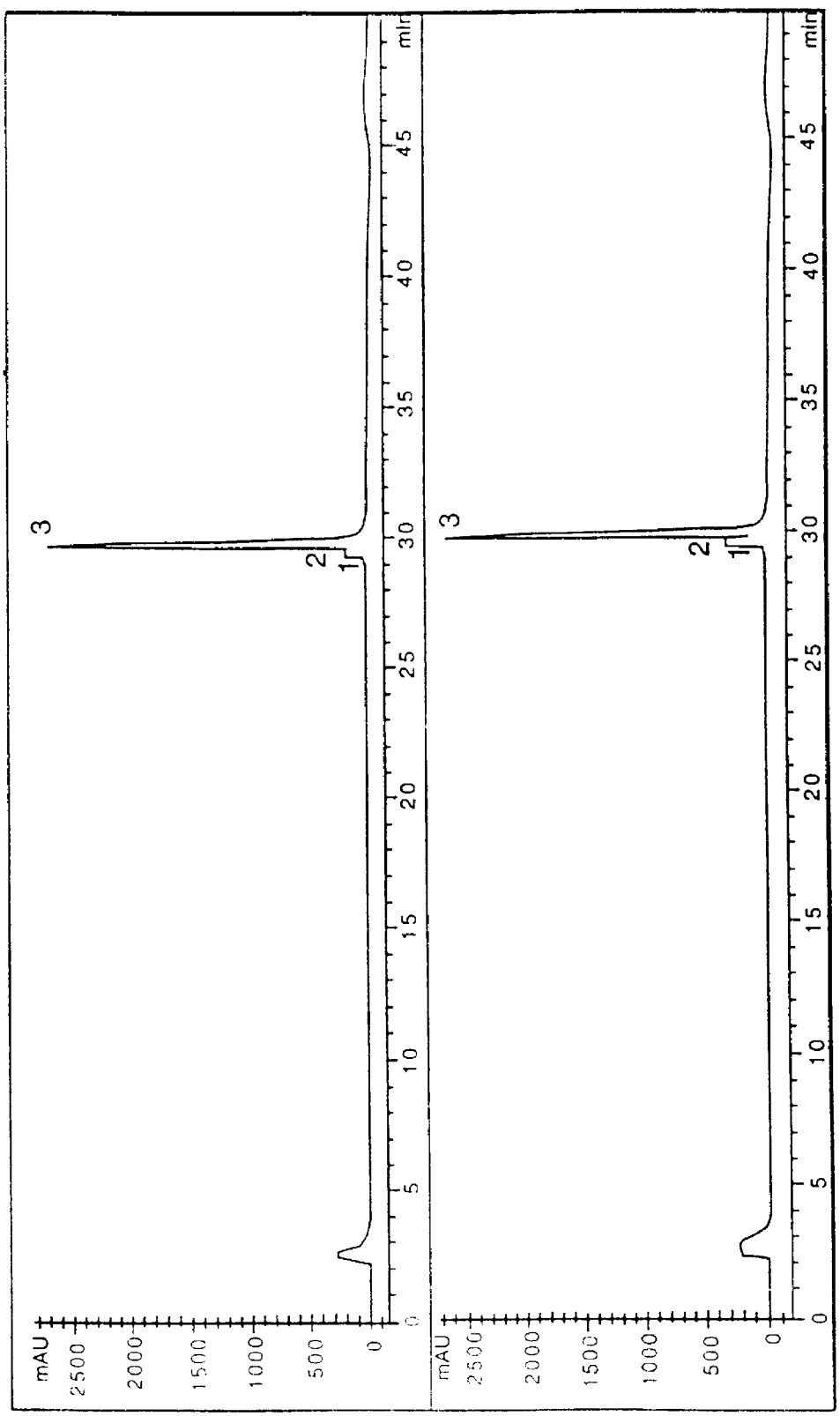
FIG. 1 is a chromatograph comparing the HPLC profile of the tgATIII of the present invention and plasma derived ATIII.

This invention is based upon the discovery that hATIII produced by the transgenic method of the present invention is structurally different than ATIII extracted from plasma (phATIII). The monosaccharide composition of the transgenically produced ATIII (tgATIII) differs in the composition and the quantity when compared to plasma derived ATIII. In particular, the glycosylation sites on the tgATIII vary considerably in contrast to phATIII which are all uniform.

EXEMPLIFICATION

Generation of the gene construct

A mammary gland-specific transgene was constructed by inserting the human Antithrombin III (hATIII) cDNA into the caprine beta casein gene (CSN2). The caprine beta casein gene was cloned as an 18.5 Kb fragment in a lambda EMBL3 vector (Roberts, et al., Gene., 1992. 121: p. 255–262). The 6.2 Kb promoter (including exon 1 and part of exon 2) was fused to the hATIII cDNA to direct high level mammary gland-specific expression. A 7.2 Kb 3' flanking region (including part of exon 7, exon 8, and exon 9) was added to the 3' end of the hATIII cDNA to help stabilize the expression levels. The 14.95 Kb transgene was excised from bacterial sequences and injected into goat embryos for the production of hATIII in goats' milk.

Identification of gene coding for the protein of interest

The hATIII cDNA was received from Dr G. ZettimeiBl (Behringwerke A.G., Marburg, Germany) in the plasmid pBAT6. The sequence of the cDNA is the same as that published by Bock, et al., Nucleic Acids Research, 1982. 10: p. 8113–8125, except for the silent nucleotide changes at bp 1096 (T–C) and bp 1417 (A–G).

Identification of regulatory sequences of interest

To direct high level tissue-specific expression of hATIII to the mammary gland of transgenic goats, the goat beta casein gene was cloned from a lambda EMBL3 goat genomic library. The goat beta casein gene is a mammary gland-specific gene which directs expression of high levels of beta casein into the milk. In goats, beta casein is thought to comprise 25–50% of the total milk proteins (~10–20 mg/ml). The goat beta casein gene was cloned from a Saanen goat genomic library and characterized in transgenic mice as described in Roberts, et al., 1992.

Cloning DNA fragments

High molecular weight goat DNA was isolated from a Saanen goat blood sample according to the procedure described by Herrmann and Frischauf, Methods Enzymology, 1987. 152: p. 180–183. The genomic DNA was partially digested with MboI and ligated into BamHI cleaved lambda EMBL3 phage arms (Stratagene, La Jolla, Calif.) by standard methods (Maniatis et al., Molecular Cloning, A Laboratory Manual, 2d, Cold Spring Harbor Laboratory Press, 1989). The Saanen goat genomic library consisted of $1.2 \times 10^6$ recombinant phage and was used to isolate the goat beta casein gene. The goat genomic library was screened using a 1.5 Kb HindIII/TthIII1 fragment encoding the entire mouse CSN2 cDNA (Yoshimura, et al., Nucleic Acids Res., 1986. 14: p. 8224) and three overlapping clones were identified. The three overlapping clones were designated EMBL 3-7, 3-8, and 3-11. Only clone 3-11 contained the entire goat beta casein gene and was used for all future analysis and vector construction (Roberts, et al., 1992).

Characterization of cloned material

The goat beta casein gene was isolated as an 18.5 Kb fragment in lambda EMBL3 phage clone designated EMBL3-11 (Roberts, et al., 1992). The fragment contains 4.2 Kb of 5' flanking region, exons 1 through 9, and 5.3 Kb of 3' flanking sequence. The gene was subcloned into pUC19 or pGEM3Z vectors. The subclones were sequenced by Sanger dideoxy sequencing to verify all intron/exon boundaries and the sequence is shown in SEQ. ID. No.: 1. All sequences are deposited with GenBank (accession Nos. M90556, M90557, M90558, M90559, M90560, M90561, and M90562).

Assembly and characterization of the gene construct.

The beta casein hATIII transgene was constructed to resemble as accurately as possible the intact goat beta casein gene. The vector was 14.95 Kb in length with 4.2 Kb of 5' flanking sequence and 5.3 Kb of 3' flanking sequence. The vector was engineered with three introns between exons 1-2, 7-8, and 8-9 to allow for splicing of the transcript. The introns were added to increase expression of the transgene (Brinster et al., Proc. Natl. Acad. Sci. USA., Devel. Biol. 85, pp. 836–840, 1988.) and the 3' flanking sequence to decrease chromosomal position effects.

To allow for the cloning of various inserts, the beta casein promoter and 3' flanking region were reassembled from the subclones with unique restriction sites in exon 2 and exon 7. To remove the initiator methionine of the goat beta casein, the plasmid Bc106 was digested with the restriction enzyme TaqI. The TaqI site restricts the plasmid Bc106 six nucleotides upstream of the initiator methionine (TaqI site marked with \*\*\*\*, FIGS. 10*a* and 10*b*). Following digestion with TaqI, the ends were filled in with Klenow DNA polymerase and a BamHI linker ligated into place. The ligation mixture was extracted with phenol-chloroform, chloroform-isoamyl alcohol, and ethanol precipitated as described in Maniatis, et al., 1989. The DNA was resuspended in digestion buffer and digested with EcoRI and BamHI. The resulting 1.5 Kb fragment was gel purified and ligated into pUC to form the plasmid Bc150. The entire available 5' region of the beta casein gene was constructed by sequential addition of fragments contained in the subclones Bc104, Bc147, and Bc103. The orientation of the Bc147 clone was verified by restriction mapping. The replacement of the 2.6Kb XbaI fragment with the XbaI fragment from Bc147 was needed to replace a 31bp deletion in the promoter between adjacent EcoRI restriction sites. To allow for the addition of the human antithrombin III cDNA, the BamHI site on the 3' end of Bc113 was converted to an XhoI site to form Bc114.

The 3' end of the goat beta casein gene was constructed in a similar fashion to the 5' end. The 1.8 Kb Bc107 clone was restricted with PpuMI to allow for the addition of a BamHI linker. The BamHI site was placed in exon 7 to include the intron between exons 7 and 8. The BamHI site is seven amino acids 5' to the termination of the goat beta casein mRNA but will have no effect on the hATIII since the cDNA for ATIII contains a termination signal. The BamHI/HindIII fragment spanning exon 7 from Bc107 was ligated into the vector Bc109 which contained the extreme 3' HindIII/SalI fragment to form Bc165. The 3' end was completed by the addition of the 4.4 Kb HindIII fragment from Bc108 to form the vector Bc118. The orientation of HindIII fragment from Bc108 was verified by restriction mapping. To allow for the addition of the hATIII cDNA, the 5' BamHI site in the vector Bc118 was changed to XhoI and the 3' SalI was converted to NotI to form Bc122.

In order to clone the entire hATIII cDNA into the goat beta casein expression vector, the 5' EcoRI restriction site was converted to an XhoI site using site-directed mutagenesis. The new vector designated pAT7 was sequenced to confirm the addition of the SalI site and the absence of any nucleotide changes in the 5' end. The hATIII cDNA was isolated as a 1.45 Kb XhoI/SalI fragment for cloning into the beta casein expression vector.

The 1.45 KB XhoI/SalI hATIII cDNA was first ligated into XhoI digested Bc114 and Bc122 to form Bc143 and Bc144, respectively. The orientation of the cDNA was confirmed by sequencing and restriction analysis. The unique SacII restriction in the hATIII cDNA allows for the directional cloning of the intact goat beta casein hATIII vector. The complete transgene was assembled by ligating the SalI/SacII fragment from Bc143 into a SalI/SacII digested Bc144. The 5' and 3' junction of the hATIII cDNA were confirmed by sequencing to ensure no mutations had occurred. The final vector (Bc6) was 14.95 Kb in length and contained 4.2 Kb of 5' flanking region, exon 1, intron 1, part of exon 2, the 1.45 Kb human AT III cDNA, part of exon 7, intron 7, exon 8, intron 8, exon 9, and 5.3 Kb of 3' flanking sequence. The transgene was excised from the pUC backbone by digestion with SalI/NotI. The Bc6 transgene directs mammary specific expression of an approximately 1.5 Kb hATIII-goat beta casein hybrid mRNA containing the 5' and 3' untranslated regions of the goat beta casein mRNA and coding region of the hATIII mRNA.

Testing and characterization of gene constructs

Transgene constructs are generally tested in a mouse model system to assess their ability to direct high levels of expression and their ability to express in a tissue-specific manner.

The Bc6 transgene was prepared for microinjection by digestion of the Bc6 plasmid with SalI/NotI, removal of the bacterial sequences by TAE agarose gel electrophoresis followed by banding of the transgene on a cesium chloride gradient according to Lacy, et al., A Laboratory Manual, 1986. Cold Springs Harbor Laboratory, N.Y. The 14.95 Kb transgene was then microinjected into mouse embryos to test the ability of the goat beta casein promoter to direct high level expression of recombinant human Antithrombin III (rhATIII) into the milk. Seventeen transgenic mouse lines were generated as determined by Southern analysis. One mouse line showed a level of expression of rhAT III of 0.7–1.0 mg/ml as determined by Western blot analysis and a thrombin inhibition assay. Based on expression results and data collected from other ongoing mouse and goat experiments, the Bc6 transgene was microinjected into goat embryos for production of transgenic goats.

Generation and characterization of transgenic animals

A founder ($F_0$) transgenic goat is defined as a viable transgenic animal resulting from embryo transfer of fertilized goat eggs that have been microinjected with a specified construct (Bc6). Four founder Bc6 goats were produced. The general methodologies that follow in this section were used to generate all transgenic goats.

Goat Species and breeds:

The transgenic goats produced for ATIII production are of Swiss origin, and are the Alpine, Saanen, and Toggenburg breeds.

Goat superovulation:

The timing of estrus in the donors was synchronized on Day 0 by 6 mg subcutaneous norgestomet ear implants (Syncromate-B, CEVA Laboratories, Inc., Overland Park, Kans.). Prostaglandin was administered after the first seven to nine days to shut down the endogenous synthesis of progesterone. Starting on Day 13 after insertion of the implant, a total of 18 mg of follicle-stimulating hormone (FSH—Schering Corp., Kenilworth, N.J.) was given intramuscularly over three days in twice-daily injections. The implant was removed on Day 14. Twenty-four hours following implant removal the donor animals were mated several times to fertile males over a two-day period (Selgrath, et al., Theriogenology, 1990. pp. 1195–1205).

Embryo collection:

Surgery for embryo collection occurred on the second day following breeding (or 72 hours following implant removal). Superovulated does were removed from food and water 36 hours prior to surgery. Does were administered 0.8 mg/kg Diazepam (Valium®), IV, followed immediately by 5.0 mg/kg Ketamine (Keteset), IV. Halothane (2.5%) was administered during surgery in 2 L/min oxygen via an endotracheal tube. The reproductive tract was exteriorized through a midline laparotomy incision. Corpora lutea, unruptured follicles greater than 6 mm in diameter, and ovarian cysts were counted to evaluate superovulation results and to predict the number of embryos that should be collected by oviductal flushing. A cannula was placed in the ostium of the oviduct and held in place with a single temporary ligature of 3.0 Prolene. A 20 gauge needle was placed in the uterus approximately 0.5 cm from the uterotubal junction. Ten to twenty ml of sterile phosphate buffered saline (PBS) was flushed through the cannulated oviduct and collected in a Petri dish. This procedure was repeated on the opposite side and then the reproductive tract was replaced in the abdomen. Before closure, 10–20 ml of a sterile saline glycerol solution was poured into the abdominal cavity to prevent adhesions. The linea alba was closed with simple interrupted sutures of 2.0 Polydioxanone or Supramid and the skin closed with sterile wound clips.

Fertilized goat eggs were collected from the PBS oviductal flushings on a stereomicroscope, and were then washed in Ham's F12 medium (Sigma, St. Louis, Mo.) containing 10% fetal bovine serum (FBS) purchased from Sigma. In cases where the pronuclei were visible, the embryos were immediately microinjected. If pronuclei were not visible, the embryos were placed in Ham's F12 containing 10% FBS for short term culture at 37° C. in a humidified gas chamber containing 5% $CO_2$ in air until the pronuclei became visible (Selgrath, et al.,Theriogenology, 1990. p. 1195–1205).

Microinjection procedure

One-cell goat embryos were placed in a microdrop of medium under oil on a glass depression slide. Fertilized eggs having two visible pronuclei were immobilized on a flame-polished holding micropipet on a Zeiss upright microscope with a fixed stage using Normarski optics. A pronucleus was microinjected with the Bc6 DNA construct in injection buffer (Tris-EDTA) using a fine glass microneedle (Selgrath, et al., Theriogenology, 1990. p. 1195–1205).

Embryo development:

After microinjection, the surviving embryos were placed in a culture of Ham's F12 containing 10% FBS and then incubated in a humidified gas chamber containing 5% $CO_2$ in air at 37° C. until the recipient animals were prepared for embryo transfer (Selgrath, et al., Theriogenology, 1990. p. 1195–1205).

Preparation of recipients:

Estrus synchronization in recipient animals was induced by 6 mg norgestomet ear implants (Syncromate-B). On Day 13 after insertion of the implant, the animals were given a single non-superovulatory injection (400 I.U.) of pregnant mares serum gonadotropin (PMSG) obtained from Sigma. Recipient females were mated to vasectomized males to ensure estrus synchrony (Selgrath, et al., Theriogenology, 1990. p. 1195–1205).

Embryo Transfer:

All embryos from one donor female were kept together and transferred to a single recipient when possible. The surgical procedure was identical to that outlined for embryo collection outlined above, except that the oviduct was not cannulated, and the embryos were transferred in a minimal volume of Ham's F12 containing 10% FBS into the oviductal lumen via the fimbria using a glass micropipet. Animals having more than six to eight ovulation points on the ovary were deemed unsuitable as recipients. Incision closure and post-operative care were the same as for donor animals (Selgrath, et al., Theriogenology, 1990. p. 1195–1205).

Monitoring of pregnancy and parturition:

Pregnancy was determined by ultrasonography 45 days after the first day of standing estrus. At Day 110 a second ultrasound exam was conducted to confirm pregnancy and assess fetal stress. At Day 130 the pregnant recipient doe was vaccinated with tetanus toxoid and Clostridium C&D. Selenium and vitamin E (Bo-Se) were given IM and Ivermectin was given SC. The does were moved to a clean stall on Day 145 and allowed to acclimatize to this environment prior to inducing labor on about Day 147. Parturition was induced at Day 147 with 40 mg of $PGF_2a$ (Lutalyse®) purchased from Upjohn Company, Kalamazoo, Mich. This injection was given IM in two doses, one 20 mg dose followed by a 20 mg dose four hours later. The doe was under periodic observation during the day and evening following the first injection of Lutalyse® on Day 147. Observations were increased to every 30 minutes beginning on the morning of the second day. Parturition occurred between 30 and 40 hours after the first injection. Following delivery the doe was milked to collect the colostrum and passage of the placenta was confirmed.

Verification of the transgenic nature of $F_0$ animals:

To screen for transgenic $F_0$ animals, genomic DNA was isolated from two different cell lines to avoid missing any mosaic transgenics. A mosaic animal is defined as any goat that does not have at least one copy of the transgene in every cell. Therefore, an ear tissue sample (mesoderm) and blood sample were taken from a two day old $F_0$ animal for the isolation of genomic DNA (Lacy, et al., A Laboratory Manual, 1986, Cold Springs Harbor, N.Y.; and Herrmann and Frischauf, Methods Enzymology, 1987. 152: pp. 180–183). The DNA samples were analyzed by the polymerase chain reaction (Gould, et al., Proc. Natl. Acad. Sci, 1989. 86: p. 1934–1938) using primers specific for hATIII and by Southern blot analysis (Thomas, Proc Natl. Acad. Sci., 1980. 77: 5201–5205) using a random primed hATIII cDNA probe (Feinberg and Vogelstein, Anal. Bioc., 1983. 132: pp. 6–13). Assay sensitivity was estimated to be the detection of one copy of the transgene in 10% of the somatic cells.

Generation and Selection of production herd

The procedures described above were utilized for production of the transgenic founder ($F_0$) goats, as well as other transgenic goats in our herd. The transgenic $F_0$ founder goats, for example, were bred to produce milk, if female, or to produce a transgenic female offspring if it was a male founder.

This transgenic founder male, was bred to non-transgenic females, and produced transgenic female offspring.

Transmission of transgene and pertinent characteristics

Transmission of the Bc6 transgene in our goat line was analyzed in ear tissue and blood by PCR and Southern blot analysis. For example, Southern blot analysis of the founder male and the three transgenic offspring showed no rearrangement or change in the copy number between generations. The Southern blots were probed with the 1.45 Kb ATIII cDNA and a 0.38 Kb probe corresponding to goat beta casein exon 7. The blots were analyzed on a Betascope 603 and copy number determined by comparison of the transgene to the goat beta casein endogenous gene.

Evaluation of expression levels

The expression level of rhATIII in the milk of transgenic animals is determined using a thrombin inhibition assay, which measures the inhibition of thrombin's ability to remove a small peptide from an artificial substrate (S2238, Kabi, Franklin Ohio). The basis for this assay is described as follows. The interaction between ATIII and thrombin amounts to rapid irreversible inhibition of the protease by ATIII in the presence of heparin. However, the interaction is very slow in the absence of heparin. Attempts to extend the range of ATIII detectable on a single standard curve reveal that ATIII can only be determined accurately in stoichiometric titration across the linear range of standard curves. At low total thrombin concentration ($0.7 \times 10^{-9}$M), the effective measuring range for ATIII is $0.15$–$0.75 \times 10^{-9}$M (~7.3–36.8 ng/ml). At high total thrombin, the effective measuring range for AT III is 0.25 to $1.25 \times 10^{-9}$M (~12–60 ng/ml) if the data are fit with a first degree polynomial, and 0.25 to $2.5 \times 10^{-9}$M (~12–120 ng/ml) if the data are fit with a second degree polynomial.

AT III ACTIVITY ASSAY

Materials:
1. 12×75 mm Glass Tubes;
2. Behring hATIII dilute to 0.5 mg/ml with $diH_2O$ ($E^{0.1\%}_{280}$=0.72);
3. Thrombin (100 units/vial diluted to 1.82 mls with 0.1 mg/ml BSA), purchased from Calbiochem, San Diego Calif.). Final Concentration 20 $\mu$g/ml;
4. Heparin (Sigma) from porcine intestinal mucosa 50 mg dissolved 5.0 mls $diH_2O$. Final Concentration 10 mg/ml;
5. Substrate (Kabi) S2238 25 mg diluted to 10 mls with $diH_2O$;
6. Dilution Buffer: 50 mM Tris, 150 mM NaCl, 0.1 mg/ml BSA pH 8.1;
7. Glacial Acetic Acid;
8. Repeat Pipettor; and
9. 37° C. circulating $H_2O$ bath.

ASSAY SET-UP

Dilution of Stocks:

1. AT III stock to 1 $\mu$g/ml: 20 $\mu$l ATIII+980 $\mu$ls dilution buffer then 100 $\mu$l+900 $\mu$l dilution buffer;
2. Heparin/Buffer: 12.5 $\mu$l Heparin+25 mls dilution buffer; and
3. Thrombin stock: 1:10 dilution into dilution buffer (2.0 mls for a 30 tube assay).

Standard Curve Set-Up

| Final Concentration AT III | Diluted AT III Stock | Dil Buffer | Heparin Buffer | Thrombin |
|---|---|---|---|---|
| 0 ng/ml | 0 $\mu$l | 100 $\mu$l | 750 $\mu$l | 50 $\mu$l |
| 5 ng/ml | 5 $\mu$l | 95 $\mu$l | 750 $\mu$l | 50 $\mu$l |
| 10 ng/ml | 10 $\mu$l | 90 $\mu$l | 750 $\mu$l | 50 $\mu$l |
| 20 ng/ml | 20 $\mu$l | 80 $\mu$l | 750 $\mu$l | 50 $\mu$l |
| 30 ng/ml | 30 $\mu$l | 70 $\mu$l | 750 $\mu$l | 50 $\mu$l |
| 40 ng/ml | 40 $\mu$l | 60 $\mu$l | 750 $\mu$l | 50 $\mu$l |
| 50 ng/ml | 50 $\mu$l | 50 $\mu$l | 750 $\mu$l | 50 $\mu$l |
| 60 ng/ml | 60 $\mu$l | 40 $\mu$l | 750 $\mu$l | 50 $\mu$l |

1. Incubate the above at 37° C. for 15 minutes;
2. Then add 100 $\mu$l of substrate to each tube using a repeat pipettor and incubate for 15 minutes at 37° C.;
3. Stop with 50 $\mu$l of glacial acetic acid to each tube; and
4. Read at 405 nm. Blank with 150 $\mu$l Buffer, 750 $\mu$l Heparin Buffer, 100 $\mu$l substrate and 50 $\mu$l Acetic acid stopped at time zero (NOT INCUBATED).

Calculations: Use a second order polynomial curve fit for the standard curve, plug A 405 nm readings into the equation. Divide by the volume of sample used in the assay tube in mls and multiply by the appropriate inverse dilution factor for the sample.

Characterization of Human ATIII Produced in the Milk of a Transgenic Goat.

TgATIII was purified from goat milk by adaptation of methods previously developed for extracting ATIII from mouse milk and human blood. Other more novel methods for separating proteins from milk are also in development. The method described is the earliest method that we utilized. Milk from one BC6 goat contained tgATIII at a concentration estimated to be 0.08 mg/ml by ELISA. Other goats with much higher expression levels (4 to 6 mg/ml) were also developed and milk from those goats was purified using similar methods. Small scale purification was performed by the following method.

ATIII Purification Process

ATIII Extraction/Clarification

Thaw Milk
Add an equal volume of 2M Arginine
Centrifuge at 8000 rpm for 30 minutes and remove the fat pad on the top
Filter through a 0.2 $\mu$m nominal polypropylene filter -continued ATIII Purification Process Dilute the conductivity to less than 20 mS/cm
(approximately a 1/7 dilution)
Expected step yield of AT III is ≥95%
Heparin-Hyper D ™ Chromatography Equilibrate with 3 column volumes of 20 mM sodium phosphate,
50 mM NaCl, pH 7.0
Load, the target operational capacity is approximately 8 mg of
ATIII/mL of resin
Wash with 4 column volumes of Equilibration Buffer
Step Elute with 4 column volumes of 20 mM sodium phosphate, 3.0M
NaCl, pH 7.0
Dilute with 9 volumes of 1.5M sodium citrate
Expected step yield of ATIII is ≥95%
Ether-Poros ™ 50 Chromatography Equilibrate with 3 column volumes of 1.40M sodium citrate, pH 7.0
Load, the target operational capacity is approximately 4 mg of ATIII/mL
of resin
Wash with 4 column volumes of Equilibration Buffer
Step Elute with 4 column volumes of 1.10M sodium citrate, pH 7.0
Expected step yield of ATIII is ≥75%
Ultrafiltration with Amicon YM10 Spiral Crossflow Concentrate to approximately 20 mg/mL (160 units/mL) and buffer exchange into 10 mM ammonium bicarbonate, pH 7.4.
Expected step yield of ATIII is ≥95%
Lyophilize Reconstitute into buffer of choice
Expected step yield of ATIII is ≥95%

Figure 2:
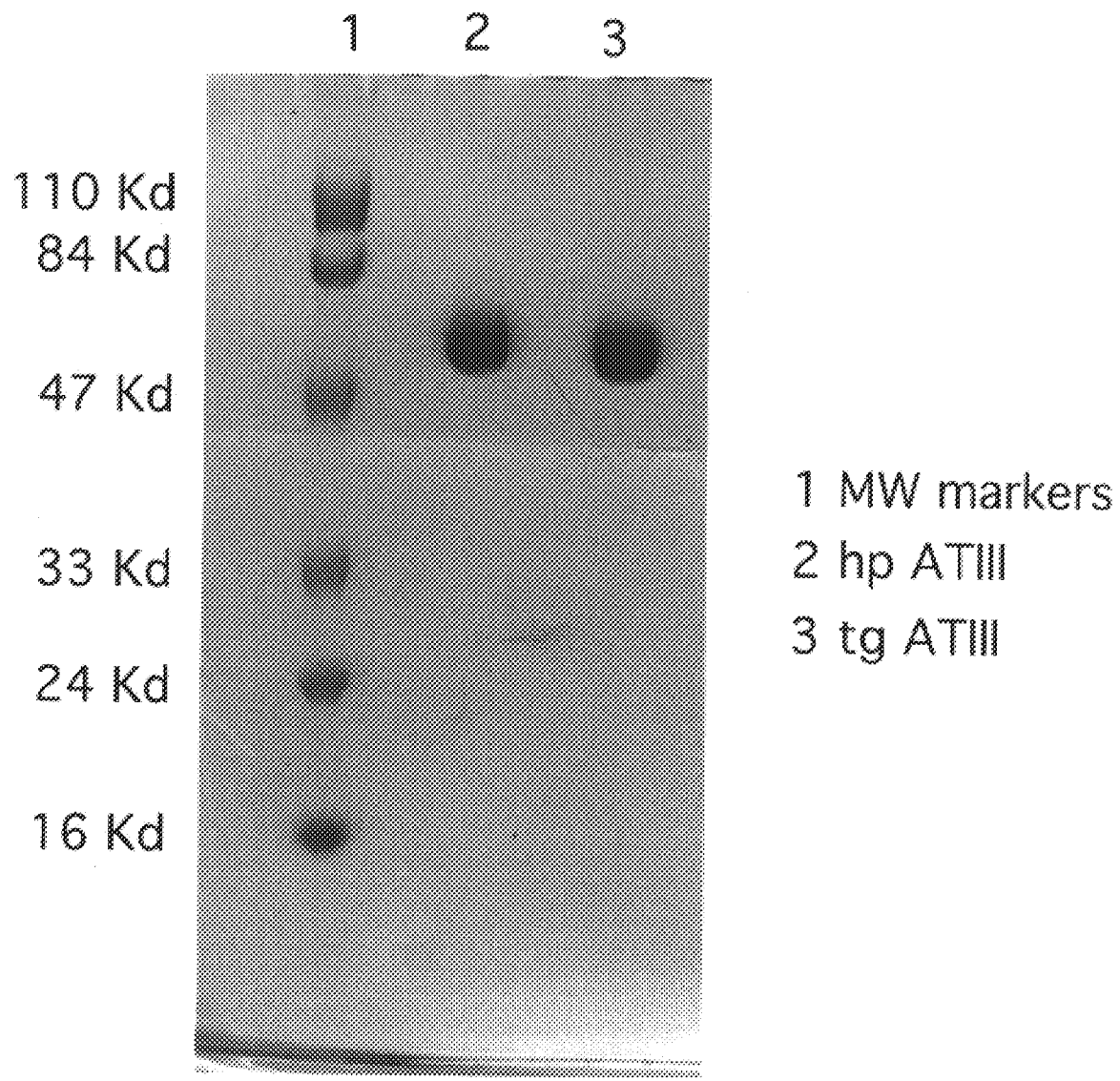
FIG. 2 is a photograph of a SDS page gel showing a greater than 98% purity of tgATIII.

A sample of the concentrated pool was examined by SDS-PAGE (10% separating gel) with a human ATIII standard for comparison and estimation of purity. The purity is estimated to be >98% (see FIG. 2.). The UV/Vis spectrum of tgATIII is indistinguishable (within experimental error) from that of plasma derived hATIII. N-terminal sequence analysis gave the predicted sequence for hATIII. Reversed phase HPLC analysis showed three peaks for goat tgATIII compared to two peaks for plasma ATIII (FIG. 1). All three peaks were found to be ATIII by N-terminal sequence analysis. Peak #1 is miniscule in the tgATIII and not apparent in the plasma derived ATIII. Peak 2 is present in both samples and varies with preparations. Peak three is the predominant peak. Examination of specific peaks from FIG. 1 following digestion with lysylendopeptidase and separation by reverse phase HPLC to create peptide maps identified the presence of oxidized methionine residues in the two early small peaks of the tgATIII. The middle peak contained oxidized methionines mainly on a single peptide (K30 on table 2), whereas the earliest peak contained oxidized methionines on most of the peptides that contained methionine. The major peak did not contain any oxidized methionines as measured by the technique being used above. The presence of oxidized methionines on this ATIII may be a function of the processing of the molecule following removal of the milk from the goat.

Monosaccharide compositional analysis indicating the amounts of fucose (Fuc), GalNac, N-Acetylglucosamine (GlcNAc), Galactose (Gal), Mannose (Man) and Sialic Acid is shown below in Table 1.

TABLE 1

| | mole sugar/mole protein | | | | | |
|---|---|---|---|---|---|---|
| Sample | Fuc | GalNAc | GlcNAc | Gal | Man | Sialic Acid |
| phATIII | 0.39 | 0.00 | 20.70 | 11.74 | 14.90 | 11.80 |
| tATIII | 3.18 | 2.39 | 14.75 | 6.44 | 18.18 | 5.21 |

Figure 3:
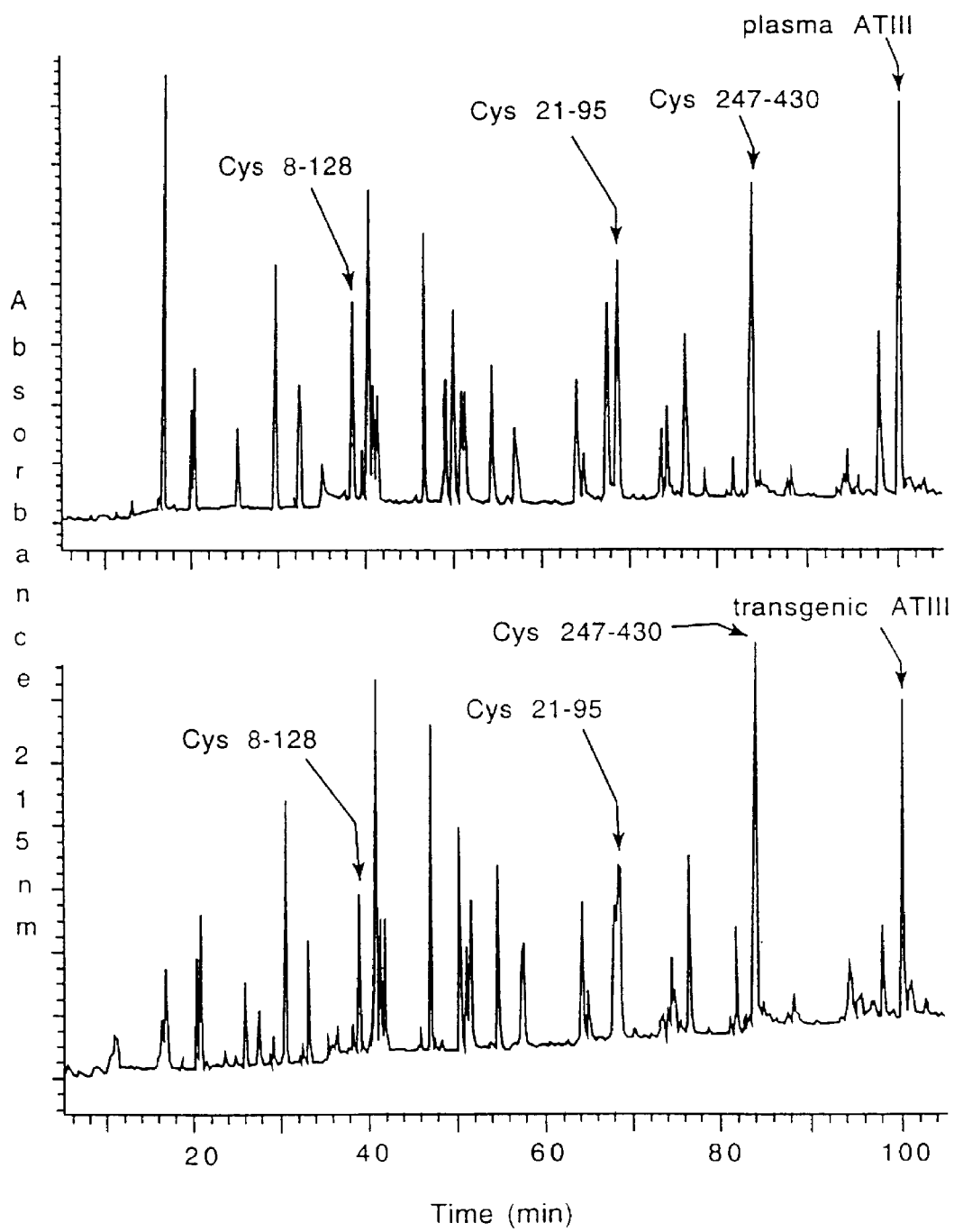
FIG. 3 illustrates that the disulfide cross-linking between phATIII and the tgATIII. The peaks labelled with the arrows are the peaks containing disulfide cross-linked peptides.

Lysylendopeptidase maps of plasma derived hATIII and tgATIII have been analyzed by liquid chromatography/mass spectrometry (LC/MS) to compare the amino acid backbone structure, the glycosylation profile and to confirm the identity of the disulfide linked peptides. For non-reduced human plasma ATIII and tgATIII, 32 of the 35 predicted peptides were identified, including the three pairs of disulfide linked peptides. The disulfide cross-linking was identical in the plasma ATIII and the tgATIII as shown in the peptide maps of the non-reduced proteins (FIG. 3). The peaks labeled with the arrows are the peaks containing disulfide crosslinked peptides. These peaks have identical retention times for each disulfide crosslinked peptide pair of each protein. The remaining peaks on the maps are identical with the exception of the glycosylated peptides. The maps of the reduced, pyridylethylated ATIII digests detail this variability more specifically.

Figure 4:
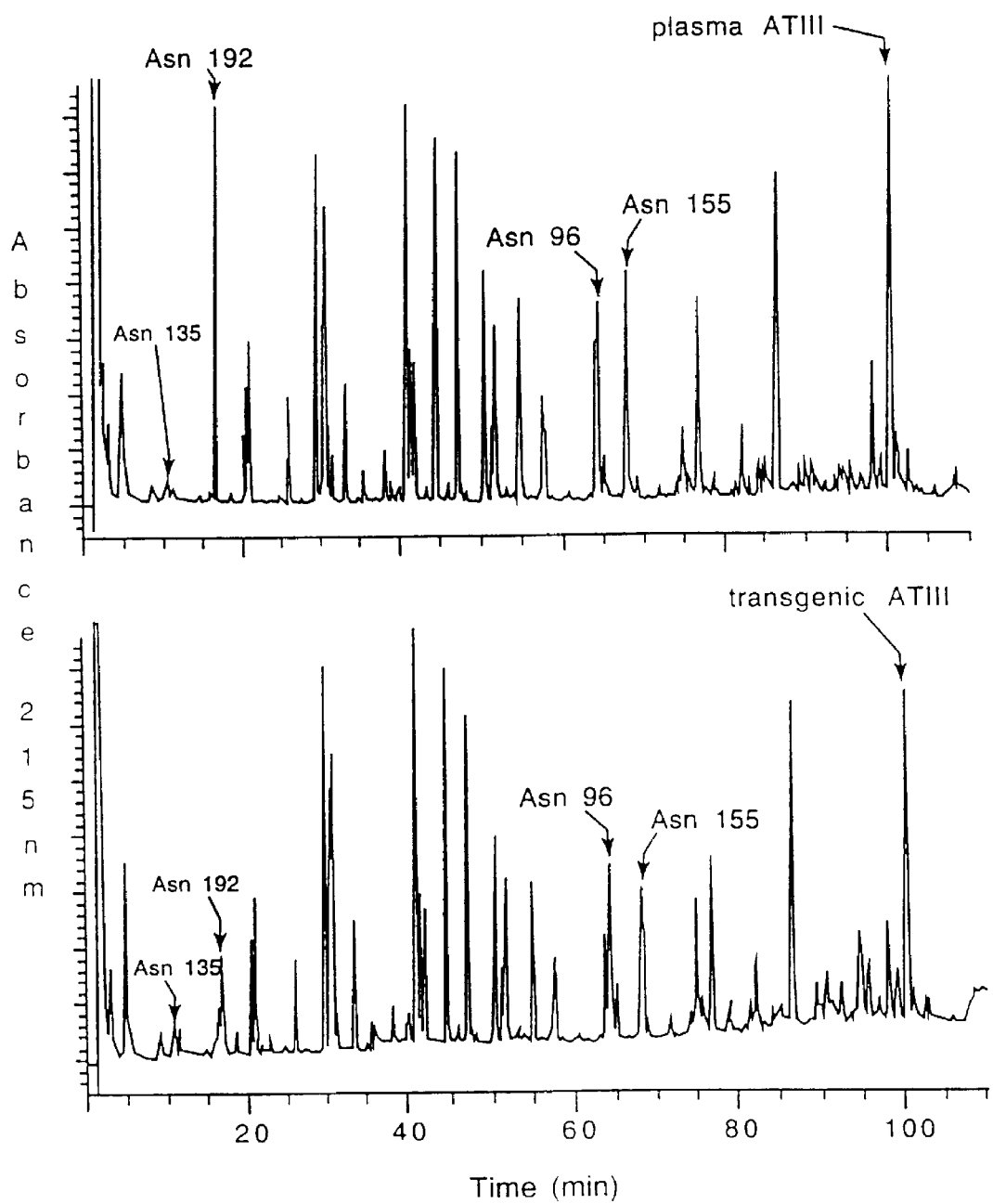
FIG. 4 shows the individual equivalent peptides of tgATIII and phATIII by mass spectrometry.

For reduced and pyridylethylated plasma and transgenic hATIII, 33 of the 35 predicted peptides were identified by LC/MS. Chromatograms of the plasma ATIII and the individual forms of the tgATIII can be seen in FIG. 4 with the identification of the individual equivalent peptides by mass spectrometry shown in Table 2 below. Again, all of the peptides are identical with the exception of the glycosylated peptides.

TABLE 2

| LC/MS ANALYSIS of ATIII PEPTIDE MAPS | | | | |
|---|---|---|---|---|
| PEPTIDE | RESIDUES | THEORETICAL MASS | phATIII | tgATIII |
| K1 | 1–11 | 1232.4 | 1232.0 | 1232.3 |
| K2 | 12–28 | 2152.6 | 2152.6 | 2152.3 |
| K3 | 29—29 | 146.2 | ID | ID |
| K4 | 30–39 | 1093.1 | 1092.9 | 1092.8 |
| K5 | 40–53 | 1699.0 | 1698.7 | 1698.7 |
| K6 | 54–70 | 1957.1 | 1956.9 | 1956.9 |
| K7 | 71–91 | 2299.6 | 2299.3 | 2299.4 |
| K8 | 92–107 | GP | GP | GP |
| K9 | 108–114 | 838.9 | 838.7 | 838.7 |
| K20 | 115–125 | 1340.5 | 1340.3 | 1340.2 |
| K11 | 126–133 | 1170.5 | 1170.1 | 1170.1 |
| K12 | 134–136 | GP | GP | GP |
| K13 | 137–139 | 320.4 | ND | ND |
| K14 | 140–150 | 1219.4 | 1219.1 | 1219.4 |
| K15 | 151–169 | GP | GP | GP |
| K16 | 170–176 | 860.0 | 860.2 | 860.0 |
| K17 | 177–188 | 1330.4 | 1330.4 | 1330.2 |
| K18 | 189–193 | GP | GP | GP |
| K19 | 194–222 | 3248.8 | 3248.8 | 3248.8 |
| K20 | 223–226 | 502.6 | 502.9 | 502.8 |
| K21 | 227–228 | 233.3 | ND | ND |
| K22 | 229–236 | 978.1 | 978.1 | 977.9 |
| K23 | 237–241 | 698.8 | 698.5 | 698.6 |
| K24 | 242–257 | 1799.0 | 1798.8 | 1798.9 |
| K25 | 258–275 | 2209.6 | 2209.3 | 2209.6 |
| K26 | 276–287 | 1314.6 | ID | ID |
| K27 | 288–290 | 372.4 | ID | ID |
| K28 | 291–294 | 417.5 | 417.3 | 417.5 |
| K29 | 295–297 | 374.5 | 374.2 | 374.2 |
| K30 | 298–332 | 4261.0 | 4261.1 | 4260.9 |

TABLE 2-continued

LC/MS ANALYSIS of ATIII PEPTIDE MAPS

| PEPTIDE | RESIDUES | THEORETICAL MASS | phATIII | tgATIII |
|---|---|---|---|---|
| K31 | 333–348 | 1849.1 | 1849.0 | 1848.9 |
| K32 | 349–350 | 233.3 | ID | ID |
| K33 | 351–370 | 2202.5 | 2202.5 | 2202.2 |
| K34 | 371–403 | 3448.9 | 3448.7 | 3448.7 |
| K35 | 404–432 | 3421.2 | 3421.2 | 3421.2 |
| K3–4 | 29–39 | 1221.3 | 1221.4 | 1221.1 |
| K26–27 | 276–290 | 1669.0 | 1668.8 | 1668.9 |
| K32–33 | 349–370 | 2417.7 | 2417.5 | 2417.6 |

GP = Glycopeptide
ND = Not detected (m/z 2+ below scan range)
ID = Incomplete digestion product
phATIII = Human Plasma ATIII
tgATIII = Transgenic (goat) Human ATIII The glycopeptide peak retention times (glycopeptide peaks are labeled with K#'s on FIG. 4) did not vary significantly from those of the plasma derived protein, but the chromatograms show that peak widening and peak splitting did occur due to the variability in the oligosaccharide residues attached to the glycopeptides.

Based on the LC/MS, peptide mapping, and carbohydrate composition data, the only differences observed between the tgATIII and the plasma derived hATIII arise due to the different patterns of glycosylation. Despite the presence of N-Acetylgalactosamine (GalNAc) in the monosaccharide analysis, no O-linked glycosylation was present on the transgenic protein, suggesting the presence of oligosaccharides different than found on the plasma derived human ATIII.

The major glycoform at each glycosylation site of the plasma derived (pATIII) is a complex type oligosaccharide and has a mass corresponding to HexNAc4, Hex5, NANA2 which is in agreement with the reported structure GlcNAc4, Man3, Gal2, NANA2. With the exception of $Asn_{155}$, located on K15, the major glycoforms on tgATIII contain oligosaccharides of the complex type. The major glycoform at each of the complex oligosaccharide containing sites on tgATIII has a mass corresponding to HexNAc4, Hex6, NANA1 which is in agreement with the structure GlcNAc4, Fuc1, Man3, Gal2, NANA1 with the second most abundant form being the disialylated form of the same structure, HexNAc4, Hex6, NANA2 which is in agreement with the structure GlcNAc4, Fuc1, Man3, Gal2, NANA2

Figure 5:
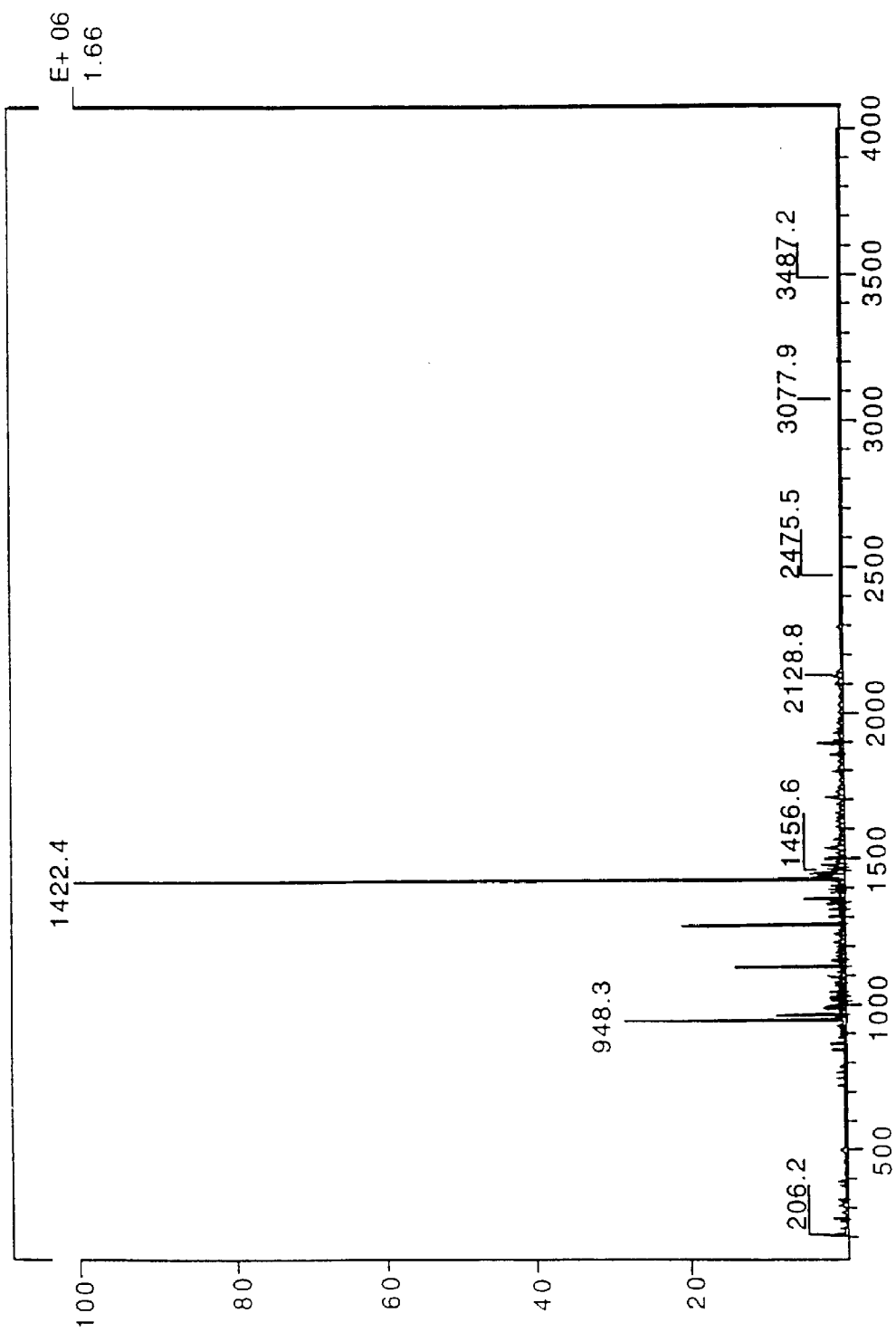
FIG. 5 illustrates the mass spectrometry data for one of the individual glycopeptide residues from plasma derived ATIII.
Figure 6:
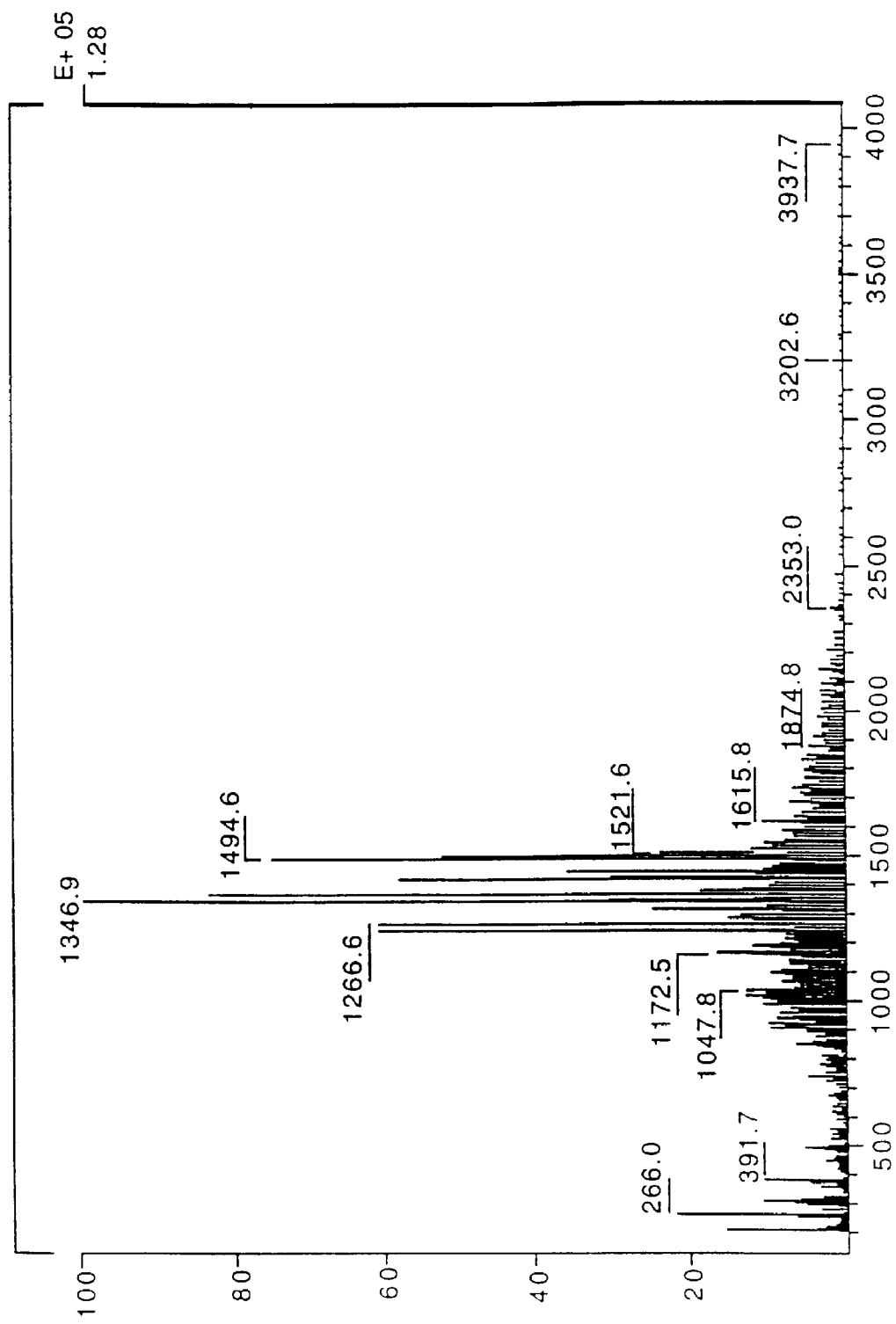
FIG. 6 shows the mass spectrometry data for the same glycopeptide residue as shown for FIG. 5, but for tgATIII.

TgATIII contains a significant amount of oligomannose type and hybrid forms at $Asn_{155}$ and only a very low level of hybrid structures at the other locations. Oligomannose type structures are more primitive structures that are remodeled into the complex type oligosaccharides in the endoplasmic reticulum. Oligomannose structures display masses ranging from Hex5 to HexNAc2, Hex9. These values agree with structures comprised of 5 up to GlcNAc2, Man9, with only the number of mannose residues varying. Hybrid oligosaccharides contain elements of complex oligosaccharides on one antenna of an individual glycosylation site and components of oligomannose type oligosaccharides on the other antenna. The N-linked glycosylation for tgATIII was much more heterogeneous than phATIII, with a higher degree of fucosylation and more varied sialylation (Table 3). Several glycoforms with a mass difference of 41 were observed by LC/MS which can be accounted for by the substitution of a Hexose residue by a HexNAc (Tables 4). In view of the monosaccharide composition (Table 1) and the lack of O-linked glycosylation (based on comparison of the observed vs theoretical mass for all peptides other than those containing an N-linked site) this could be accounted for by the substitution of one or more galactose residues by GalNAc. This result was confirmed by fragmentation analysis mass spectroscopy of isolated glycopeptides. FIG. 5 is an example of the mass spectrometry data for one of the individual glycopeptide residues from phATIII. It's pattern is fairly simple. In contrast, FIG. 6 is an example of the same glycopeptide from tgATIII. The increased complexity of the pattern is obvious, and can be deciphered into specific structures as described above.

Figure 7:
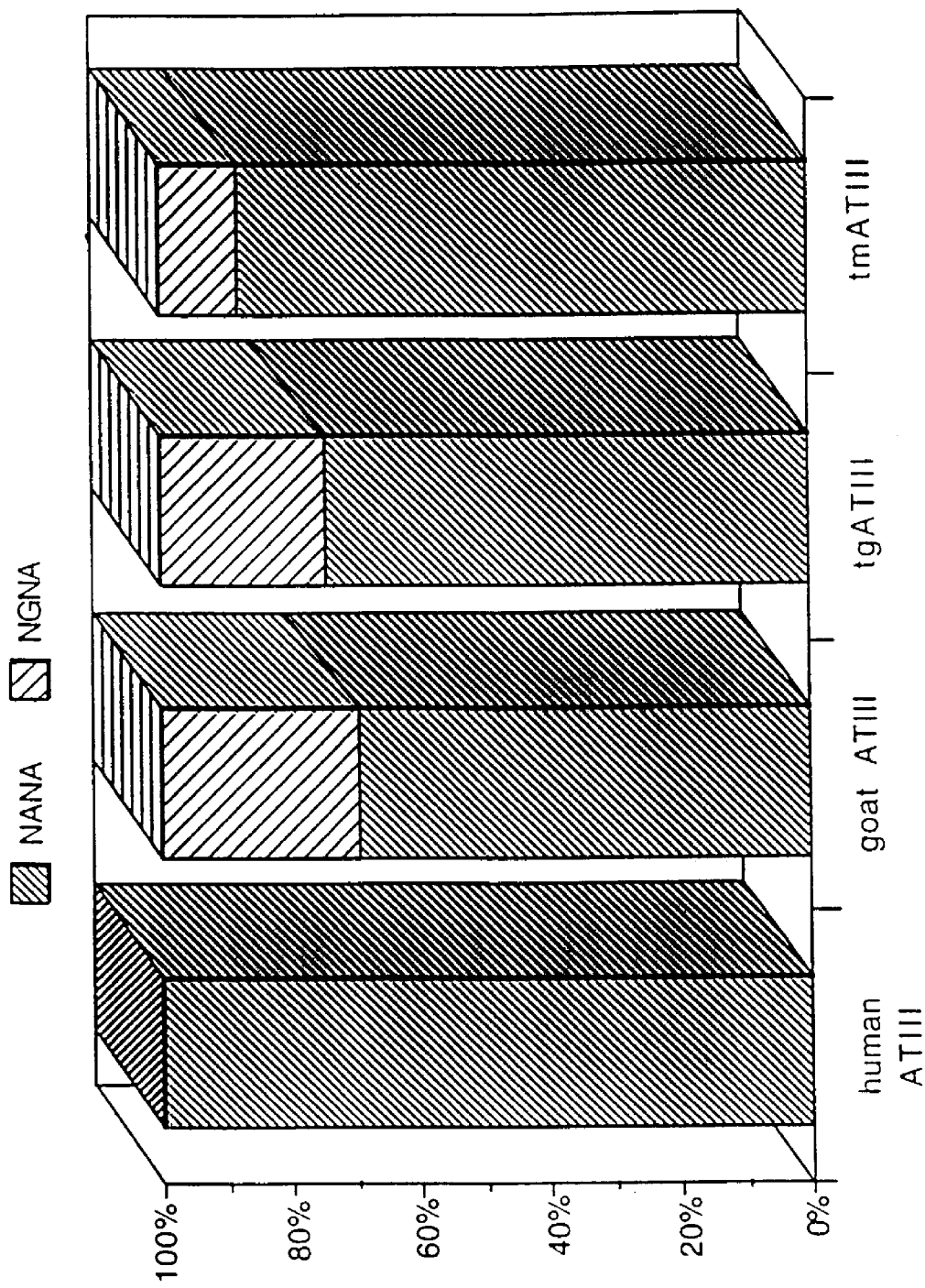
FIG. 7 illustrates the sialic acid composition of human ATIII, goat ATIII, tgATIII, and transgenic mouse ATIII (tmATIII).

Several glycoforms with mass differences of 16 mass units were also identified. The difference is explained by the presence of an oxidized form of sialic acid, N-Glycolyineuraminic acid (NGNA) in place of N-Acetyineuraminic acid (NANA). NGNA is a common form of sialic acid found in goats. Approximately 25% of the sialic acids found in tgATIII are NGNA. Approximately 25% of goat plasma ATII sialic acid is NGNA (FIG. 7).

Thus, we have determined that; (1) one of the four glycosylation sites on tgATIII has mainly high mannose (oligomannose) and hybrid type oligosaccharide structures, whereas the phATIII has biantenarry, complex oligosaccharides on each of the four sites; (2) the complex oligosaccharides of tgATIII are not fully sialylated, whereas the phATIII oligosaccharides are fully sialylated; (3) the tgATIII has a percentage of its sialic acid that is NGNA whereas the phATIII has only NANA; and (4) tgATIII contains N-acetylgalactosamine on its N-linked oligosaccharides and the phATIII does not; and (5) the tgATIII has fucose on its proximal GlcNAc on each of the three sites having complex oligosaccharides, whereas the phATIII has only a very small amount of fucose on any site.

Figure 8:
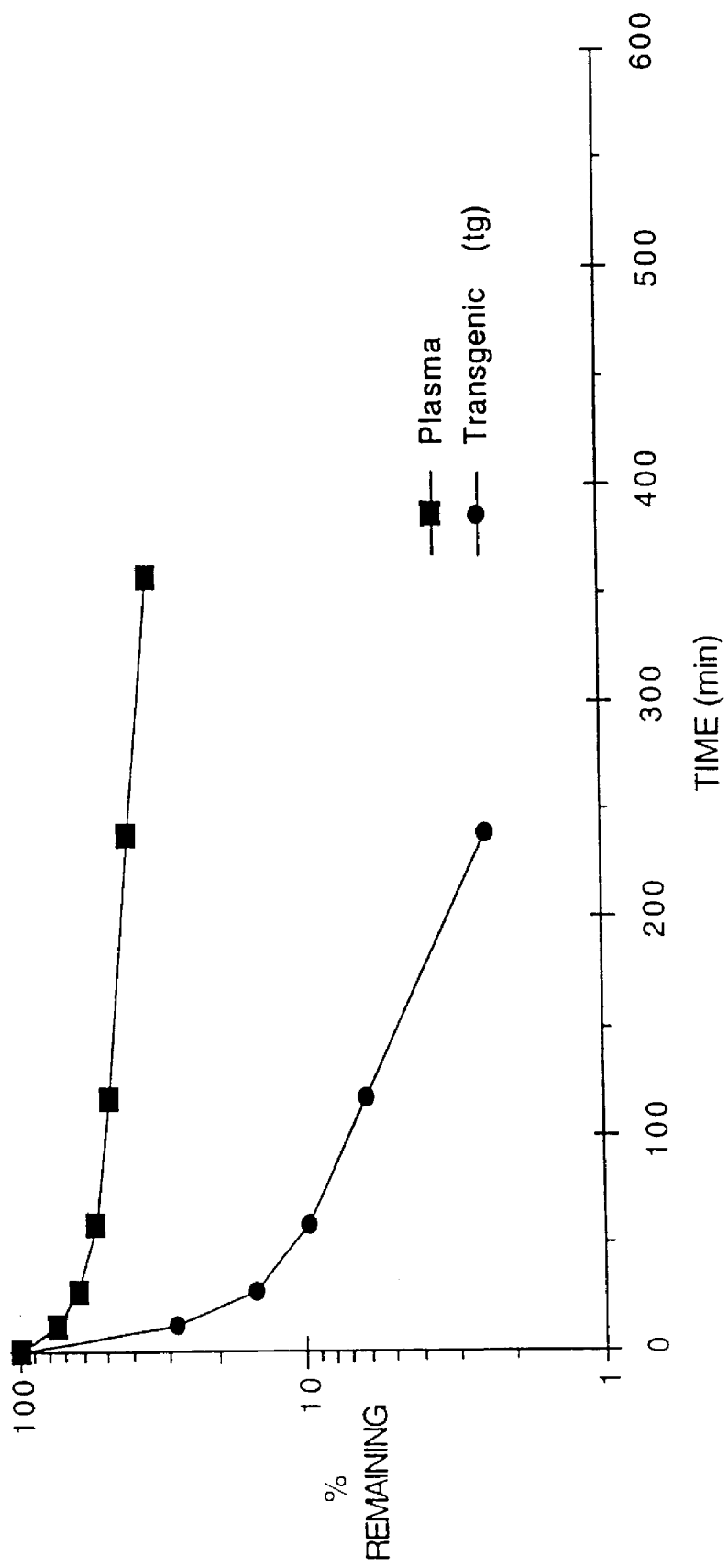
FIG. 8 shows a graph comparing the clearance rate of phATIII and tgATIII in mice.
Figure 9:
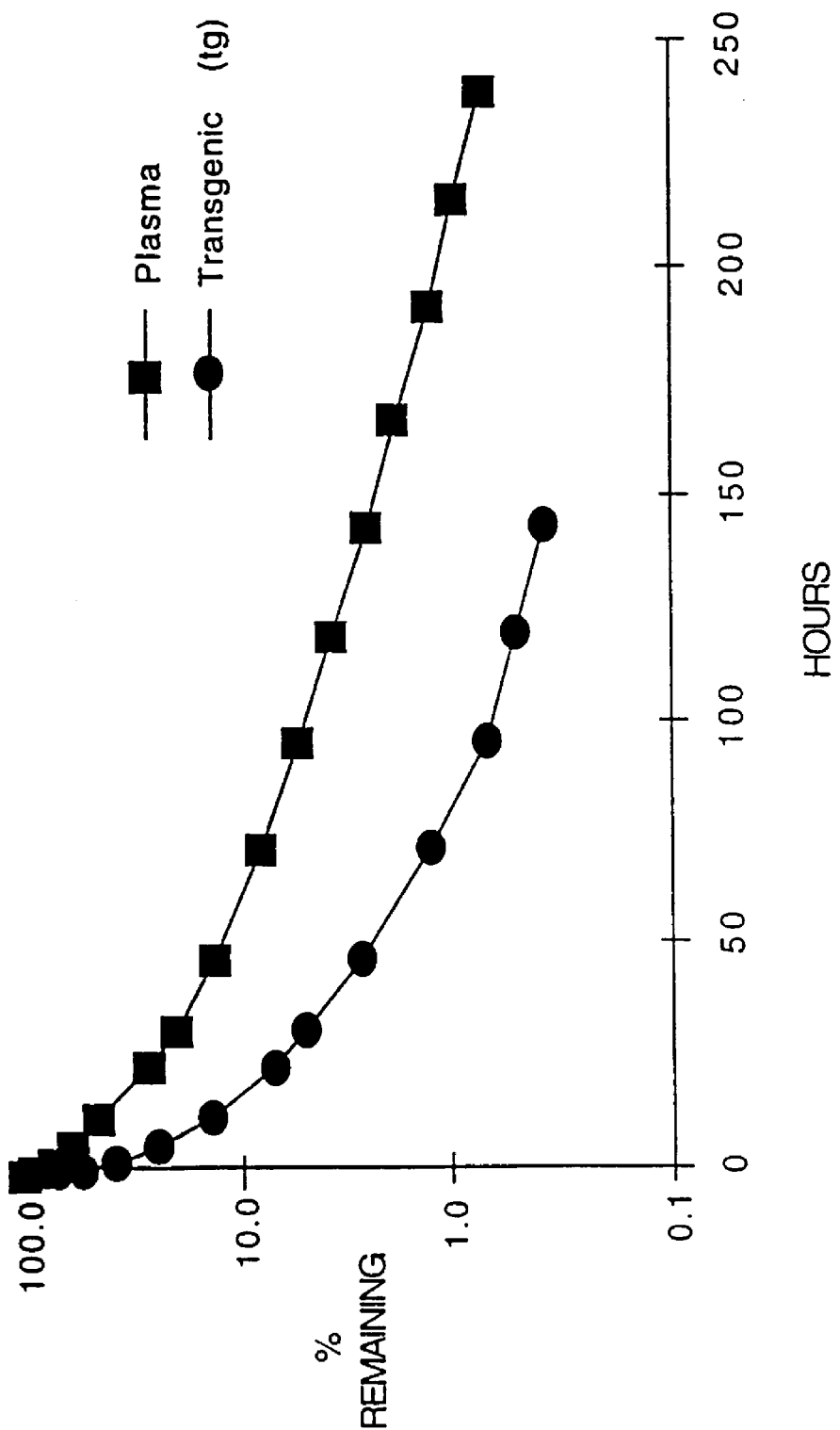
FIG. 9 shows a graph comparing the clearance rate of phATIII and tgATIII in monkey.

The tgATIII exhibits a faster clearance time in rabbits, mice and monkeys than does phATIII. Twenty μg samples of test ATIII was injected via the tail vein and residual ATIII determined using an ELISA assay which has little cross reactivity with mouse ATIII. The pattern shown in FIG. 8 for clearance in mice mimics the pattern found for the same materials in rabbits. The clearance appears to be bimodal and is approximately 10 times faster than for hATIII. In vivo clearance was also examined in a monkey model system. Both trace and high levels of radioiodinated ATIII were injected and detected in plasma samples by counting in a gamma counter. The clearance pattern of tgATIII in monkeys indicated only a 4 to 5-fold faster clearance (FIG. 9) from the circulation than the phATIII and could also be defined by a biphasic mechanism.

Early experiments indicate that the tgATIII may have a stronger affinity for heparin than the phATIII. This would be important since ATIII inhibits thrombin at inflamation or injury sites by binding to heparan sulfate in the endothelial layer of the vasculature. Once bound its affinity for thrombin is enhanced 1000-fold and it binds to and irreversibly inhibits thrombin.

Equivalents

Those skilled in the art will recognize, or be able to ascertain, using no more than routine experimentation, many equivalents to the specific embodiments of the invention described herein. Such equivalents are intended to be encompassed by the following claims:

The invention claimed is:

1. A method for producing human antithrombin III in goat milk, comprising:

a. producing a transgenic goat that expresses in mammary tissue a transgene which encodes a human antithrombin III, wherein the human antithrombin III is secreted into the milk produced by the transgenic goat;

b. collecting milk from the transgenic goat which milk contains the human antithrombin III; and c. isolating the human antithrombin III from the collected milk, wherein the human antithrombin III isolated from milk has faster clearance time and an increased affinity for heparin both compared to human antithrombin III isolated from human plasma.

2. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:
   a) monosaccharide glycosylation comprising GalNac;
   b) no O-linked glycosylation;
   c) faster plasma clearance time and an increased affinity for heparin both compared to human antithrombin III that is isolated from human plasma.

3. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:
   a) monosaccharide glycosylation comprising Fuc, GalNAc, GlcNAC, Gal, Man, and NANA/NGNA;
   b) no O-linked glycosylation;
   c) faster plasma clearance time and an increased affinity for heparin both compared to human antithrombin III that is isolated from human plasma.

4. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:
   a) monosaccharide glycosylation comprising oligomannose and/or hybrid oligosaccharide structures;
   b) no O-linked glycosylation;
   c) faster plasma clearance time and an increased affinity for heparin both compared to human antithrombin III that is isolated from human plasma.

5. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) monosaccharide glycosylation comprising primarily an oligomannose or hybrid type structure on one site and complex oligosaccharide on the remaining 3 sites, b) no O-linked glycosylation;

c) faster plasma clearance time and an increased affinity for heparin both compared to human antithrombin III that is isolated from human plasma.

6. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) a monosaccharide composition which is partially sialylated;

b) no O-linked glycosylation;

c) faster plasma clearance time and an increased affinity for heparin both compared to human antithrombin III that is isolated from human plasma.

7. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) a monosaccharide composition comprising sialic acid which includes NGNA;

b) no O-linked glycosylation;

c) faster plasma clearance time and an increased affinity for heparin both compared to human antithrombin III that is isolated from human plasma.

8. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) monosaccharide glycosylation comprising a fucose on its proximal GlcNAc on each of the sites having oligosaccharides;

b) no O-linked glycosylation;

c) faster plasma clearance time and an increased affinity for heparin both compared to human antithrombin III that is isolated from human plasma.

9. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) monosaccharide glycosylation comprising N-acerylglucosamine and mannose;

b) no O-linked glycosylation;

c) faster plasma clearance time and an increased affinity for heparin both compared to human antithrombin III that is isolated from human plasma.

10. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) monosaccharide glycosylation comprising N-acetylglucosamine, galactose and mannose;

b) no O-linked glycosylation;

c) faster plasma clearance time and an increased affinity for heparin both compared to human antithrombin III that is isolated from human plasma.

11. A glycosylated human antithrombin III, wherein a glycosylated human antithrombin III is made by the method of isolating the glycosylated human antithrombin III from milk, wherein the milk is collected from a transgenic goat, which goat expresses in mammary tissue a transgene encoding human antithrombin III and wherein the human antithrombin III is secreted into the milk produced by the transgenic goat; and wherein the glycosylated human antithrombin III has the following properties:

a) monosaccharide glycosylation comprising N-acetylglucosamine, N-acetylgalactosamine and mannose;

b) no O-linked glycosylation;

c) faster plasma clearance time and an increased affinity for heparin both compared to human antithrombin III that is isolated from human plasma.

12. The glycosylated human antithrombin III of any one of claim 2, 3, 4, 5, 6, 7, 8, 9, 10 or 11, wherein the plasma clearance time of the transgenically produced antithrombin III is at least about 10 times faster than the plasma clearance time of the naturally occurring plasma antithrombin III.

13. The glycosylated human antithrombin III of any one of claim 2, 3, 4, 5, 6, 7, 8, 9, 10 or 11, wherein the affinity for heparin of the transgenically produced antithrombin III results in at least about 1000 fold enhanced affinity for thrombin as compared to the naturally occurring plasma antithrombin III.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3515 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v ) FRAGMENT TYPE: N-terminal ( x i ) SEQUENCE DESCRIPTION: SEQ ID NO:1:

```
AGAATTTACC CCAAGATCTC AAAGACCCAC TGAATACTAA AGAGACCTCA TTGTGGTTAC      60
AATAATTTGG GGACTGGGCC AAAACTTCCG TGCATCCCAG CCAAGATCTG TAGCTACTGG     120
ACAATTTCAT TTCCTTTATC AGATTGTGAG TTATTCCTGT TAAAATGCTC CCCAGAATTT     180
CTGGGGACAG AAAAATAGGA AGAATTCATT TCCTAATCAT GCAGATTTCT AGGAATTCAA     240
ATCCACTGTT GGTTTTATTT CAAACCACAA AATTAGCATG CCATTAAATA CTATATATAA     300
ACAGCCACTA AATCAGATCA TTATCCATTC AGCTTCTCCT TCACTTCTTC TCCTCTACTT     360
TGGAAAAAAG GTAAGAATCT CAGATATAAT TTCAGTGTAT CTGCTACTCA TCTTTATTTT     420
GGACTAGGTT AAAATGTAGA AAGAACATAA TTGCTTAAAA TAGATCTTAA AAATAAGGGT     480
GTTAAGATA  AGGTTTACAC TATTTTCAGC AGATATGTTA AAAAATAGAA GTGACTATAA     540
AGACTTGATA AAAATTATAG GTGACTGCAA TTTTTGCCAT GAGGTTTGCA GGATCTTGGT     600
TCCCTGACCA GGGATCAAAC CTGCACTCCC CTGGAAGCAT GGAGTCTTGG ACATTTGTAT     660
TATACACTAT CTTTGGTTCC TTTTAAAGGG AAGTAATTTT ACTTAAATAA GAAAATAGAT     720
TGACAAGTAA TACGCTGTTT CCTCATCTTC CCATTCACAG GAATCGAGAG CCATGAAGGT     780
CCTCATCCTT GCCTGTCTGG TGGCTCTGGC CATTGCAAGA ACAAAGAGGT AAATACAGAA     840
AAAATGTTGA AATAATAGAC TAGTACTGTC TGCCTATGTG TAGAAATCAC ATTACCAACA     900
TCATAAATGT ATAAATAATG CACAATCTCA GATTTATTTT TTAATGCTAA GAAAGTCATT     960
TATGTTCATC CACTATCTCA ACAGTATCCT ATAGGACCAC AACTCTGGGT CAAGTGCTTT    1020
CTATAGTATT GTACCATCTG TACCATCAAT TCCTAAAGAA AAAGGAAAAG AAACCAATAA    1080
GCAACAGACC AACAAGAAGG AACACAGACA AGAACAAAAA ATGAGTAATA TTGTACAAAT    1140
ACAATTGCAC GCTGCAGGAA CTAAAGTGTT TTTTTTCTC  TCTCTTTTA  GCAGGAAGAA    1200
CTCAATGTAG TCGGTGAGGT AAGATGATTT TTATACAAAG AAAAAAATTA ATTTAACTGT    1260
AAAATAGTAA CAGACTCTGA TGATCTAGCA GAAAACTCAG CTAATTGTCA ATTTTTATTT    1320
TTCCTTTATA GACTGTGGAA AGCCTTTTCA AGCAGTGAGG TAAGATAATG TTCATTCAGA    1380
GGCAATTTCC CAGATTTAGA GCAATAAAAC ACTGTATTAT CTTTTTGTGT TACATTAATT    1440
GGCAACCCAC TCCAGTACTC TTGACAAATA TGAATTTTTC TTTAAAGCTA AACCTGATTT    1500
TATTTTTATT TTTCCAAAGG AATCTATTAC ACACATCAAT AAGGTAAAAC CTTCATATTT    1560
AAACGTATCA TTTTTAAAAA TTTCATGTTT GATTTTTATA AACAGCATTT CTTTATGTGT    1620
```

| | | | | | | |
|---|---|---|---|---|---|---|
| GATTTTTTTT | TTTACCAGAA | AATTGAGAAG | TTTCAAAGTG | AGGAACAACA | GCAAACAGAG | 1680 |
| GTAATTTGTT | TCACTATGAG | TATATTTTGA | GAAGTATTAT | GAAACATAAC | ACATAAAGA | 1740 |
| TTTATAATAA | TTATGTTCAG | TCTAAGAATG | GTAATATAAG | TGTCAGTGTA | AGAAATGAAA | 1800 |
| ACTTTGACAA | AATGAAAATA | TTTTAAAGAT | AGAAACACAT | TTTTAAACAC | ATAATCAAAT | 1860 |
| TTCAGAGTAT | AGAATAAATA | CCCAAGAATA | ACTACTGGTA | TATTCATTTT | ACTAATGGTA | 1920 |
| TACCTGGCTT | TAATAAATGC | ATATTAGTAG | GAACAATTCC | AGACTAGGGA | CTGTGATCCC | 1980 |
| CTTATTCTAA | TGATGGATAT | GCTGATGAAA | GACAGTAGGG | TGACAGTGTG | GCACTAATCC | 2040 |
| TAATAAATGG | AAGATTTTCT | TTCTCTCTCT | TCACTGAATT | ATGTTTTAAA | AAGAGGAGGA | 2100 |
| TAATTCATCA | TGAATAACAA | TTATAACTGG | ATTATGGACT | GCAAAGGCAT | TGGTTTTCCT | 2160 |
| TCTTTCCAGG | ATGAACTCCA | GGATAAAATC | CACCCCTTTG | CCCAGGCACA | AAGTCTCTAG | 2220 |
| TCTATCCCTT | CACTGGGCCC | ATCCCTAACA | GCCTCCACA | AAACATCCTG | CTGCTCTTAC | 2280 |
| TCAAACCCCT | GTGGTGGTGC | CGCCTTTCCT | TCAGCCTGAA | ATAATGGGAG | TCCTTGCCAA | 2340 |
| AGTGAAGGAG | ACTATGGTTC | CTAAGCACAA | AGAAATGCCC | TTCCCTAAAT | ATCCAGTTTG | 2400 |
| AGCCCTTTAC | TGAAAGCCAG | AGCCTGACTC | TCACTGATGT | TGAAAAGCTG | CACCTTCTTT | 2460 |
| CTCTGCCTCT | GGTCCAGTCT | TGGATGCACC | AGCCTCCCCA | GCCTCTTTCT | CCAACCGTCA | 2520 |
| TTGTTTCCTC | CTCAGTCCGT | GCTGTCCCTT | TCTCAGCCCA | AAGTTCTGCC | TGTTCCCCAG | 2580 |
| AAAGCAGTGC | CCCAGAGAGA | TATGCCCATC | CAGGCCTTTC | TGCTGTACCA | GGAGCCTGTA | 2640 |
| CAATTGGTCC | TGTCCGGGGA | CCCTTCCCTA | TTCTTGTAAG | TCTAAATTTA | CTAACTGTGC | 2700 |
| TGTGGTTAAC | TTCTGATGTT | TGTATGATAT | TTGAGTAATT | AAGAGCCCTA | CAAAAAAATC | 2760 |
| AATAATGAAT | GGTTCCAAAA | TAAGCATAGC | TGAGATTAAT | GATTCTCAGC | ATTAGTTATA | 2820 |
| AATAGAATAA | GCTGGAAAAC | CTTCACCTCC | CCTCCACCAC | CAGATCCCAA | AAACAAAATA | 2880 |
| CTGAAGATGC | TTATTTCAAT | ACTCAGGGAA | AATTTCTTG | CCAAAAGGC | AAGAATTGTA | 2940 |
| TAATTCATTC | ACTTATTTTA | TTTTTTTTAA | TTTTTAAGGT | CTAAGAGGAT | TTCAAAGTGA | 3000 |
| ATGCCCCCTC | CTCACTTTTG | GTCAAATTGG | AAATGGGGGT | GAGATGAAGA | GTTATAACAT | 3060 |
| ATAACTAAAT | GGACATTGTT | CTCTATTCCA | CAGAATTGAC | TGCGACTGGA | AATATGGCAA | 3120 |
| CTTTTCAATC | CTTGCATCAT | GCTACTAAGA | TAATTTTTAA | ATGAGTATAC | ATGGAACAAA | 3180 |
| AAATGAAACT | TTATTCCTTT | ATTTATTTTA | TGCTTTTTCA | TCTTAATTTG | AATTTGAGTC | 3240 |
| ATAACCATA | TACTTTCAAA | ATGTTAATTC | AACATTAGCA | TAAAAGTTCA | ATTTTAACTT | 3300 |
| GGAAATATCA | TGAACATATC | AAATTATGTA | TAAAAATAAT | TTCTGGAATT | GTGATTATTA | 3360 |
| TTTCTTTAAG | AATCTATTTC | CTAACCAGTC | ATTTCAATAA | ATTAACCCTT | AGGCATATTT | 3420 |
| AAGTTTTCTT | GTCTTTATTA | TATTTTTAAA | AATGAAATTG | GTCTCTTTAT | TGTTAACTTA | 3480 |
| AATTTATCTT | TGATGTTAAA | AATAGCTGTG | GAAAA | | | 3515 |

(2) INFORMATION FOR SEQ ID NO:2:

(i) SEQUENCE CHARACTERISTICS:
(A) LENGTH: 222 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Val Leu Ile Leu Ala Cys Leu Val Ala Leu Ala Ile Ala Arg
 1               5                  10                  15

Glu Gln Glu Glu Leu Asn Val Val Gly Glu Thr Val Glu Ser Leu Ser
```

-continued

|  |  |  | 20 |  |  |  | 25 |  |  |  | 30 |  |  |
|---|---|---|---|---|---|---|---|---|---|---|---|---|---|
| Ser | Ser | Glu 35 | Glu | Ser | Ile | Thr | His 40 | Ile | Asn | Lys | Lys | Ile 45 | Glu | Lys | Phe |
| Gln | Ser 50 | Glu | Glu | Gln | Gln | Gln | Thr 55 | Glu | Asp | Glu | Leu 60 | Gln | Asp | Lys | Ile |
| His 65 | Pro | Phe | Ala | Gln | Ala 70 | Gln | Ser | Leu | Val | Tyr 75 | Pro | Phe | Thr | Gly | Pro 80 |
| Ile | Pro | Asn | Ser | Leu 85 | Pro | Gln | Asn | Ile | Leu 90 | Pro | Leu | Thr | Gln | Thr 95 | Pro |
| Val | Val | Val | Pro 100 | Pro | Phe | Leu | Gln | Pro 105 | Glu | Ile | Met | Gly | Val 110 | Pro | Lys |
| Val | Lys | Glu 115 | Thr | Met | Val | Pro | Lys 120 | His | Lys | Glu | Met | Pro 125 | Phe | Pro | Lys |
| Tyr | Pro 130 | Val | Glu | Pro | Phe | Thr 135 | Glu | Ser | Gln | Ser | Leu 140 | Thr | Leu | Thr | Asp |
| Val 145 | Glu | Lys | Leu | His | Leu 150 | Pro | Leu | Pro | Leu | Val 155 | Gln | Ser | Trp | Met | His 160 |
| Gln | Pro | Pro | Gln | Pro 165 | Leu | Ser | Pro | Thr | Val 170 | Met | Phe | Pro | Pro 175 | Gln | Ser |
| Val | Leu | Ser | Leu 180 | Ser | Gln | Pro | Lys | Val 185 | Leu | Pro | Val | Pro 190 | Gln | Lys | Ala |
| Val | Pro | Gln 195 | Arg | Asp | Met | Pro | Ile 200 | Gln | Ala | Phe | Leu | Leu 205 | Tyr | Gln | Glu |
| Pro | Val 210 | Leu | Gly | Pro | Val | Arg 215 | Gly | Pro | Phe | Pro | Ile 220 | Leu | Val |  |  |